United States Patent [19]

Kadin et al.

[11] 4,031,217

[45] June 21, 1977

[54] 1-OXO-1H-6-SUBSTITUTED-PYRIMIDO(1,2-a)-QUINOLINE-2-CARBOXYLIC ACIDS AND ESTERS USEFUL AS ANTIULCER AGENTS

[75] Inventors: Saul B. Kadin; Peter F. Moore, both of New London, Conn.

[73] Assignee: Pfizer Inc., New York, N.Y.

[22] Filed: Aug. 10, 1976

[21] Appl. No.: 713,145

Related U.S. Application Data

[62] Division of Ser. No. 594,766, July 10, 1975.

[52] U.S. Cl. .............................................. 424/251
[51] Int. Cl.² .................................. A61K 31/505
[58] Field of Search .................................. 424/251

[56] References Cited

OTHER PUBLICATIONS

Richardson et al., *J. Med. Chem.*, vol. 15 (1972) pp. 1203–1206.

*Primary Examiner*—Paul M. Coughlan, Jr.
*Attorney, Agent, or Firm*—Connolly and Hutz

[57] ABSTRACT

As antiulcer agents, a series of 1-oxo-1H-6-substituted pyrimido[1,2-a]quinoline-2-carboxylic acids and esters of the formula

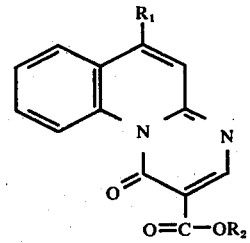

wherein $R_1$ is alkoxy having from one to two carbon atoms or piperidino; and $R_2$ is hydrogen or alkyl having from one to four carbon atoms; the pharmaceutically acceptable acid addition salts of those compounds wherein $R_1$ is piperidino, and the pharmaceutically acceptable cationic salts of those compounds wherein $R_2$ is hydrogen.

7 Claims, No Drawings

1-OXO-1H-6-SUBSTITUTED-PYRIMIDO(1,2-a)-QUINOLINE-2-CARBOXYLIC ACIDS AND ESTERS USEFUL AS ANTIULCER AGENTS

This application is a division of application Ser. No. 594,766 filed July 10, 1975.

BACKGROUND OF THE INVENTION

1. Field of the Invention

This invention relates to pyrimido[1,2-a]quinoline-2-carboxylic acids and derivatives thereof and to their use as antiulcer agents. More particularly, it relates to 1-oxo-1H-6-substitutedpyrimido[1,2-a]quinoline-2-carboxylic acids, salts and esters thereof wherein the substituent is methoxy, ethoxy or piperidino which are useful as antiulcer agents.

2. Description of the Prior Art

Chronic gastric and duodenal ulcers, collectively known as peptic ulcers, are a common affliction for which a variety of treatments have been developed. The treatment depends upon the severity of the ulcer and may range from dietary and medical (drug) treatment to surgery. A wide variety of drugs have been used to treat ulcers; the most recent of which to gain widespread attention is carbenoxolone sodium, the disodium salt of the hemisuccinate of glycyrrhetinic acid. It is reported to prevent formation of and to accelerate healing of gastric ulcers in animals, including humans ("Carbenoxolone Sodium: A Symposium," J. M. Robson and F. M. Sullivan, Eds., Butterworths, London, 1968). However, its use is accompanied by undesirable aldosterone-like side effects, such as marked antidiuretic and sodium-retaining activity and, oftentimes, potassium loss, such that continued therapy with this agent often leads to hypertension, muscle weakness and, ultimately, congestive heart failure.

An effective treatment of peptic ulcers is, therefore, desirable. One which will effectively act upon gastric ulcers, without causing the aldosterone-like side effects observed with carbenoxolone, is especially desirable.

The synthesis of a 1H-pyrimido[1,2-a]quinoline appears to have first been reported by Antaki et al., J. Chem. Soc., pages 551–555 (1951), who condensed 2-chloroquinoline with ethyl β-amino crotonate in the presence of anhydrous potassium carbonate and a trace of copper bronze to produce 1-oxo-1H-3-methyl-pyrimido[1,2-a]quinoline. No utility for the compound was reported.

Antaki, J. Am. Chem. Soc., 80, 3066-9 (1958), reports the condensation of 2-aminoquinoline and ethylethoxymethylenecyanoacetate to give ethyl 2-quinolylaminomethylenecyanoacetate which when distilled under reduced pressure afforded 1-oxo-1H-pyrimido[1,2-a]quinoline-2-carbonitrile. The compound demonstrated antischistosomal action.

Richardson et al., J. Med. Chem., 15, 1203–6 (1972) describe ethyl 1-oxo-1H-pyrimido[1,2-a]quinoline-2-carboxylate and report it to be inactive as an antimicrobial agent. When tested for antiulcer activity by the method described herein, it was found to be inactive via the oral route of administration.

Gupta et al., Indian J. Chem., 9, 201–206 (1971) report the preparation of ethyl 1-oxo-1H-6-hydroxypyrimido[1,2-a]quinoline-2-carboxylate and its investigation as a hypoglycemic agent. However, the compound described therein is believed to be incorrectly identified since it differs in chemical properties from the named compound prepared by the method described in this application. Ethyl 1-oxo-1H-6-hydroxypyrimido[1,2-a]quinoline-2-carboxylate when tested for antiulcer activity by the method described herein exhibited no activity by the oral route of administration.

SUMMARY OF THE INVENTION

It has now been found that compounds having the formula

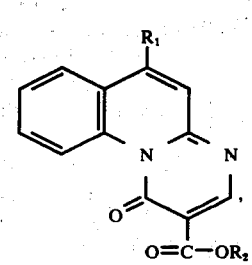

the pharmaceutically-acceptable cationic salts of those compounds wherein $R_2$ is hydrogen and the pharmaceutically-acceptable acid addition salts of those compounds wherein $R_1$ is piperidino exhibit potent antiulcer activity. In the above formula, $R_1$ is selected from the group consisting of alkoxy having from one to two carbon atoms and piperidino; and $R_2$ is selected from the group consisting of hydrogen and alkyl having from one to four carbon atoms.

By the term "pharmaceutically-acceptable cationic salts" is intended salts such as the alkali metal salts, e.g., sodium and potassium, alkaline earth metal salts such as calcium and magnesium; aluminum salts; ammonium salts; and salts with organic bases, e.g., amines such as triethylamine, tri-n-butylamine, piperidine, triethanolamine, diethylaminoethylamine, N,N'-dibenzylethylenediamine and pyrrolidine.

DETAILED DESCRIPTION OF THE INVENTION

The compounds of this invention are readily prepared by condensation of the appropriate 2-amino-4-($R_1$-substituted)quinoline with the appropriate dialkyl ethoxymethylenemalonate to produce the corresponding intermediate dialkyl 4-($R_1$-substituted)-2-quinolylaminomethylenemalonate which is then cyclized to the desired alkyl 1-oxo-1H-6-($R_1$-substituted)-pyrimido[1,2-a]-quinoline-2-carboxylate.

The condensation is carried out by heating a stoichiometric mixture of the 2-aminoquinoline reactant and the dialkyl ethoxymethylenemalonate at a temperature of from about 80° to about 125° C. Lower temperatures are not desirable because the reaction proceeds at too slow a rate. Higher temperatures can be used but appear to offer no advantages. The reaction is thus conveniently carried out as a melt. It can, of course, be conducted in a solvent or mixture of solvents; for example, ethanol, N,N-dimethylformamide, acetonitrile. However, from a practical standpoint a solvent appears unnecessary.

The condensation, when conducted under the above conditions, produces the intermediate dialkyl 4-($R_1$-substituted)-2-quinolylaminomethylenemalonate. This intermediate is then cyclized, preferably thermally, to the corresponding alkyl 1-oxo-1H-6-($R_1$-substituted)-pyrimido[1,2-a]quinoline 2-carboxylate. The cyclization is accomplished by heating the intermediate dialkyl 4-($R_1$-substituted)-2-quinolaminomethylenemalonate to a temperature of from about 175° to about 250° C. until cyclization is essentially complete, usually in about 1 to 2 hours. The cyclization is advantageously achieved by heating the intermediate in a suitable reaction-inert diluent; that is, in a compound which permits control of the reaction temperature, is stable to the relatively high temperatures employed and which does not react with the starting material or the products of cyclization. Representative of such diluents are high boiling hydrocarbons such as perhydronaphthalene, mineral oil, diethylbenzene, acetic anhydride containing sulfuric acid, diphenyl ether and diphenyl, especially that which contains 26.5% diphenyl and 73.5% diphenyl ether and is sold under the trademark Dowtherm A.

It is evident that the condensation and cyclization steps can be conducted in a single operation without the need for separating the intermediate dialkyl 4-($R_1$-substituted)-2-quinolylaminomethylenemalonate simply by employing a sufficiently high reaction temperature. The overall reaction is advantageously carried out in a suitable diluent to permit close control of the reaction temperature.

The favored procedure comprises the two steps of the condensation and cyclization described above. Isolation of the intermediate compound and subsequent purification thereof before cyclization, generally afford a better quality cyclized product. The esters, intermediates for corresponding acids, are prepared by choice of the appropriate dialkyl ethoxymethylenemalonate according to the preferred method of preparation described above. Alternatively, the esters are prepared by a base-catalyzed transesterification process. The process comprises treating a lower alkyl ester (a compound wherein $R_2$ is alkyl) with an alkanol, preferably in the presence of a catalytic amount of a base (i.e., from about 5 to about 20% by weight based upon the alkanol used) such as triethylamine or calcium hydroxide, in air at a temperature of from about 20° to about 50° C. Higher temperatures can be used but appear to offer no advantage.

The compounds wherein $R_1$ is alkoxy are also conveniently prepared by the Williamson reaction between the appropriate alkyl 1-oxo-1H-6-chloro(or bromo)-pyrimido[1,2-a]quinoline-2-carboxylate and the appropriate alkanol ($R_1OH$) as exemplified herein.

Compounds wherein $R_1$ is piperidino are prepared by reaction of the appropriate alkyl 1-oxo-1H-6-chloro(or bromo)pyrimido[1,2-a]quinoline-2-carboxylate with piperidine in a 1:2 molar ratio in a reaction-inert solvent, such as ethanol or other alcohol, at a temperature of from about 50° to 100° C.

The 2-amino-4-alkoxy substituted quinoline reactants are readily prepared by reaction of the corresponding 2-amino-4-hydroxyquinoline with the appropriate lower alkyl ester of an arylsulfonic acid, such as a lower alkyl-p-toluenesulfonate or a lower alkyl ester of sulfuric acid. Alternatively, they are prepared by reaction of a metal salt—usually the sodium salt—of the appropriate 2-amino-4-hydroxyquinoline with the appropriate lower alkyl halide. The amino group is protected by acetylation, if necessary, to avoid alkylation.

Acid addition salts of compounds of formula I wherein $R_1$ is piperidino are readily made by treating the free base form of the compound with the appropriate acid in a reaction-inert solvent and recovering the acid salt by filtration or other appropriate means.

The compounds described herein are effective antiulcer agents via the intraperitoneal and oral routes of administration against gastric ulcers. These products not only accelerate healing of such ulcers but also prevent formation of ulcers and decrease gastric acid output in animals, including humans. They can, therefore, be said to be useful for the control of gastric ulcers. The incidence of side effects, e.g., aldosterone-like fluid retention and electrolyte disturbances, attendant with the use of these compounds, is relatively low or nonexistent. alone The valuable products of this invention can be administered alonr or in combination with a pharmaceutical carrier selected on the basis of the chosen route of administration and standard pharmaceutical practice. For example, they can be administered orally in the form of tablets containing such excipients as polyvinylpyrrolidone, a Carbowax (nonvolatile, solid polyethylene glycols available from Carbide and Carbon Chemicals Corporation), expecially Carbowax 6000, starch, milk sugar, etc., or in capsules alone or in admixture with the same or equivalent excipients. They may also be administered orally in the form of elixirs or oral suspensions which may contain flavoring or coloring agents or be injected parenterally; that is, for example, intramuscularly or subcutaneously. For parenteral administration, they are best used in the form of a sterile solution which may be either aqueous, such as water, isotonic dextrose, isotonic saline, Ringer's solution; or non-aqueous, such as fatty oils of vegetable origin (cotton seed, peanut oil, corn, sesame) and other non-aqueous vehicles which will not interfere with the therapeutic efficiency of the preparation and are non-toxic in the volume or proportion used (glycerol, propylene, glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol, etc.; buffering agents, as well as local anesthetics and inorganic salts to afford desirable pharmacological properties.

For both oral and intraperitoneal administration, a dosage range of from about 150 mg. to about 300 mg. per day is effective. The dosage level can, with careful supervision, range up to as high as about 2 grams per day. Propylene glycol is a suitable and convenient carrier or diluent for intraperitoneal use. Carbowax 6000 is a favored excipient for oral use. Compositions containing from about 50 to about 90% by weight of polyvinylpyrrolidone or Carbowax 6000 are especially effective for oral administration. Higher or lower amounts of excipient can, of course, be used but appear to offer no advantages over these proportions. For intraperitoneal use, the polyvinylpyrrolidone formulations are suspended in carriers such as water, or in saline solution containing 1% carboxymethylcellulose and 0.1% Tween 80 (polyoxyethylene ethers of partial esters of fatty acids and hexitol anhydrides derived from sorbitol, available from Atlas Chemical Industries, Inc.). The watersoluble products of this invention are conveniently administered in water solution.

The effectiveness of the products of this invention as antiulcer agents is determined by the stressed rat assay as follows:

Cold-Restraint Stressed Rat

Non-fasted female rats (Charles River C-D strain) weighing 70–140 gms. are administered the drug or carrier (control animals) intraperitoneally (in saline solution containing 1% carboxymethylcellulose and 0.1% Tween 80) or orally (in water) 3 hours before being lightly anesthetized with ether and taped in the supine position to individual sheets of plexiglass. After recovery from anesthesia, the restrained animals are positioned horizontally in a refrigerator maintained at 10° –12° C. and 3 hours later sacrificed by cervical dislocation. The abdomen of each rat is opened, the pylorus clamped, the stomach inflated with saline via an oral tube, the esophagus clamped and the stomach excised. The stomachs are placed in a 0.4% formaldehyde solution for approximately 30 seconds to harden the outer layers and facilitate examination. Each stomach is then cup open along the greater curvature and the glandular portion (hind stomach) examined for damage. The number of gastric erosions, their severity and the color of the stomachs is recorded. The Mann-Whitney-Wilcoxon rank sum test is used to compare the median number of gastric erosions in the control group with the median number of gastric erosions in each drug-treated group to determine if they are statistically different. (Dixon et al., "Introduction to Statistical Analysis," 3rd Ed., McGraw-Hill Book Company, New York, pp. 344–347, 1969).

The effect of the products of this invention on renal excretion of water and electrolytes in rats is determined in the following manner:

Renal Studies

Fasted female rats (Charles River Sprague-Dawley CD, 114–127 g.) are given either vehicle [5 ml./kg. of a formulation consisting of carboxymethyl cellulose (10 g.), sodium chloride (9 g.), Tween 80 (1 g.), water (to 1000 ml.)] or 1-oxo-1H-6-ethoxypyrimido[1,2-a]quinoline-2-carboxylic acid (10 mg./kg. orally, po) or carbenoxolone (100 mg./kg. intraperitoneally, ip). One hour later, the rats are given a saline load (25 ml./kg., po) and are placed in metabolism cages and total urine output collected for five hours. 1-Oxo-1H-6-ethoxypyrimido[1,2-a]quinoline-2-carboxylic acid, when given at 10 mg./kg. po to female rats one hour prior to administration of a 25 mg./kg. po saline load, did not alter the volume of urine collected over a five-hour period. Carbenoxolone at 100 mg./kg. ip, under the same conditions, caused a highly significant decrease in the urine volume collected. From these observations, it may be inferred that in clinical use, 1-oxo-1H-6-ethoxypyrimido[1,2-a]quinoline-2-carboxylic acid would not be expected to cause the edema and hypertension seen in humans treated with carbenoxolone. (Tween 80, a complex mixture of polyoxyethylene ethers of mixed partial esters of sorbitol anhydrides available from the Atlas Powder Co.)

| Treatment | Urine Vol. ml./5 hr. mean (SD) | Relative Value (Test/Control) | P Value |
|---|---|---|---|
| Control | 2.45 (.55) | 1 | — |
| Carbenoxolone (100 mg./kg. ip) | .13 (.11) | 0.05 | <.001 |
| 1-oxo-1H-6-ethoxy-pyrimido[1,2-a]quinoline-2-carboxylic acid | 2.83 (.53) | 1.15 | N.S. |

Compounds having the above formula wherein $R_2$ is ethyl and $R_1$ is methoxy or piperidino exhibit statistically significant antiulcer activity by the oral route of administration at dosage levels of 10 mg./kg. and the compound of the formula wherein $R_2$ is hydrogen and $R_1$ is ethoxy exhibits statistically significant antiulcer activity at a dose of 3 mg./kg. as well.

Their gastric antisecretory effect in pouch dogs (Heidenhain) is determined by the following procedure.

Gastric antisecretory activity is studied in overnight fasted, conscious Heidenhain pouch dogs (F) using pentagastrin, histamine or food to stimulate acid output. Pentagastrin or histamine is administered as a continuous infusion into a superfical leg vein at doses earlier determined to stimulate near maximal acid output from the gastric pouch. Food stimulus consists of ½ can of Ken-L-Ration (approx. 220 g.) per dog; dogs weighing 9–12.5 kg. are used. Gastric juice is collected at 30 minute intervals following the start of a histamine or pentagastrin infusion or the ingestion of a standard food meal. A total of ten collections are made for each dog during an experiment. Drug is administered orally after the third gastric juice collection,. All sample volumes are recorded and acid concentration is determined by titrating sample aliquots (1.0 ml.) to pH 7.4 with 0.1N NaOH using a pH meter (Radiometer) and autoburette. The drug is given orally after placing it in gelatin capsules.

1-Oxo-1H-6-ethoxypyrimido[1,2-a]quinoline-2-carboxylic acid inhibited pentagastrin stimulated acid output 47% compared with pre-drug control levels following an oral dose of 50 mg./kg. No effect on food stimulated acid output or histamine stimulated acid output at oral doses of 100 mg./kg. was exhibited by this compound.

EXAMPLE I

1-Oxo-1H-6-methoxypyrimido[1,2-a]quinoline-2-carboxylic Acid

A. A mixture of 2-amino-4-methoxyquinoline (34 g., 0.196 mole) and diethyl ethoxymethylenemalonate (46.8 g., 0.216 mole) is heated on a steam bath. A clear melt forms within about ten minutes and within about 20 minutes begins to resolidify. The mixture is heated a total of 45 minutes and is then cooled. The product, diethyl 4-methoxy-2-quinolylaminomethylenemalonate, is crystallized from ethanol (350 ml.) as a fluffy solid; m.p. 136.5°–137.5° C.

Analysis: Calc'd for $C_{18}H_{20}N_2O_5$: C, 62.78; H, 5.85; N, 8.14%. Found: C, 62.72; H, 6.10; N, 8.34%.

B. To Dowtherm A (350 ml.) at 100° C. is added the product from A (55 g., 0.16 mole) and the resulting clear yellow solution heated to 230°–233° C. for 1.75 hours. The reaction mixture is cooled, diluted with ethyl acetate (500 ml.) and then extracted with 1N hydrochloric acid (3 × 120 ml.). The extracts are combined, made basic with 20% ammonium hydroxide and chilled to precipitate the product. It is filtered and recrystallized successively from ethanol, benzene-cyclohexane (1:1) and ethanol to give 15.5 g. of the ethyl ester as yellow crystals; m.p. 130°–130.5° C.

Analysis: Calc'd for $C_{16}H_{14}N_2O_4$: C, 64.42; H, 4.73; N, 9.39%. Found: C, 64.38; H, 4.80; N, 9.54%.

C. The procedure of Example I-B is repeated but starting with 3.5 g. of diethyl 4-methoxy-2-quinolylaminomethylenemalonate. The product is recovered by cooling the reaction mixture, diluting it with cyclohexane (150 ml.) to precipitate the crude product as a brown gummy material. It is obtained in crystalline form by heating the diluted reaction mixture to boiling and filtering the hot mixture. Upon cooling, the ethyl ester precipitates as yellow crystals and is separated by filtration. Yield = 1.1 g. Further purification is achieved by recrystallizing it from ethanol.

Hydrolysis of the Ester

A mixture of ethyl 1-oxo-1H-6-methoxypyrimido[1,2-a]quinoline-2-carboxylate (3.0 g.) and concentrated hydrochloric acid (60 ml.) is heated on a steam bath for a half hour. It is then cooled and filtered to give 0.87 g. of the title product. It is recrystallized from N,N-dimethylformamide; m.p. 219° C. (dec.).

Analysis: Calc'd for $C_{14}H_{10}N_4O_2$: C, 62.22; H, 3.73; N, 10.37%. Found: C, 61.60; H, 3.73; N, 10.30%.

EXAMPLE II

1-Oxo-1H-6-Ethoxypyrimido[1,2-a]quinoline-2-carboxylic Acid

The procedures of Examples I-A and I-C are repeated but beginning with 2-amino-4-ethoxyquinoline in place of 2-amino-4-methoxyquinoline to give the ethyl ester of the title compound; m.p. 143°–145° C.

Hydrolysis of the ester according to the procedure of Example I affords the acid; m.p. 205° C. (dec.).

Analysis: Calc'd for $C_{15}H_{12}N_4O_2$: C, 63.37; H, 4.26; N, 9.86%. Found: C, 63.16; H, 4.33; N, 9.91%.

EXAMPLE III

The following compounds are prepared from the appropriate 2-amino-4-(substituted)quinolines and the appropriate lower alkyl ethoxymethylenemalonates by the procedures of Example I-A and I-C. The acid forms are produced by the hydrolysis procedure of Example I.

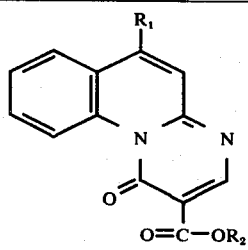

| $R_1$ | $OR_2$ |
|---|---|
| $OC_2H_5$ | $OCH_3$ |
| $OCH_3$ | $O-n-C_3H_7$ |
| $OCH_3$ | $O-n-C_4H_9$ |
| $OCH_3$ | $O-i-C_4H_9$ |
| $OC_2H_5$ | $O-i-C_3H_7$ |
| $OCH_3$ | $OCH_3$ |
| $OC_2H_5$ | $O-n-C_4H_9$ |

EXAMPLE IV

Ethyl 1-Oxo-1H-6-Chloropyrimido[1,2-a]Quinoline-2-Carboxylate

A. A mixture of 2-amino-4-chloroquinoline (15.5g. 0.087 mole) and diethyl ethoxymethylenemalonate (20.8g., 0.096 mole) is heated on a steam bath for 45 minutes. Isopropanol (75 ml.) is added to the hot clear melt which is then cooled. The product separates and is filtered, washed with isopropanol and dried. Yield = 26.0g. of white solid; m.p. 108.5°–109.5° C. It is used directly in step B without further purification.

Recrystallization from ethanol affords an analytical sample, m.p. 109°–110° C.

Analysis: Calcd. for $C_{17}H_{17}N_2O_4Cl$: C, 65.37; H, 5.16; N, 8.97%. Found: C, 65.18; H, 5.17; N, 9.07%.

B. The intermediate diethyl 4-chloro-2-quinolylaminomethylenemalonate from step A (26 g.) is added to Dowtherm A (75 ml.) at 100° C. The resulting clear solution is heated to 235°–237° C. for 80 minutes and then cooled. Hexane (100 ml.) is added to the reaction mixture and the product which precipitates recovered by filtration, washed with hexane and dried. It is recrystallized from acetonitrile, m.p. 178°–179° C.

Analysis: Calcd. for $C_{15}H_{11}N_2O_3Cl$: C, 59.51; H, 3.66; N, 9.26%. Found: C, 59.02; H, 3.85; N, 9.09%.

Repetition of the above procedure but using the appropriate dialkyl ethoxymethylenemalonate in place of the diethyl ester affords the methyl, n-propyl, isopropyl and n-butyl esters of the title compound.

EXAMPLE V

Ethyl 1-Oxo-1H-6-Ethoxypyrimido[1,2-a]Quinoline-2-Carboxylate

A mixture of p-toluenesulfonic acid monohydrate (20 mg.) and ethyl 1-oxo-1H-6-Chloropyrimido[1,2-a]quinoline-2-carboxylate (1.5g.) in ethanol (75 ml.) is heated at reflux for 24 hours. The solvent is removed under reduced pressure and the residue partitioned between 3N hydrochloric acid (25 ml.) — ethyl acetate (100 ml.). The phases are separated and the ethylacetate phase extracted with 3N hydrochloric acid (2 × 20 ml.). The acid extracts are combined, made basic with 20% ammonium hydroxide and the resulting precipitate recovered by filtration (235 mg.). It is recrystallized from cyclohexane (30 ml.)—benzene (5 ml.); m.p. 143°–144° C.

Analysis: Calcd. for $C_{17}H_{16}N_2O_4$: C, 65,37; H, 5.16; N, 8.97%. Found: C, 64.18; H, 5.17, N, 9.07%.

EXAMPLE VI

The procedure of Example V is repeated but using the appropriate products of Example V and the appropriate alcohols to give:

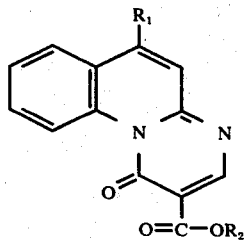

| $R_1$ | $R_2$ |
|---|---|
| $OCH_3$ | $OC_2H_5$ |
| $OCH_3$ | $OCH_3$ |
| $OCH_3$ | $O-n-C_4H_9$ |
| $OC_2H_5$ | $O-n-C_3H_7$ |

EXAMPLE VII

Ethyl-1-Oxo-1H-6-Hydroxypyrimido[1,2-a]Quinoline-2-carboxylate

A mixture of ethyl 1-oxo-1H-6-methoxypyrimido[1,2-a]quinoline-2-carboxylate (596 mg., 2.0 millimoles) in 30% HBr in acetic acid (20 ml.) is heated at reflux for 3.5 hours. The reaction mixture is then cooled and the product, 1-oxo-1H-6-hydroxypyrimido[1,2-a]quinoline-2-carboxylic acid, filtered off. It is recrystallized from N,N-dimethylformamide. Yield = 160 mg. m.p. 268.5° C (dec.)

Analysis: Calcd.: for $C_{13}H_8O_4N_2$: C, 60.94; H, 3.14; N, 10.94%. Found: C, 60.40; H, 3.20; N, 10.92%.

The acid is esterified by refluxing with excess ethanol in the presence of 3% hydrochloric acid as catalyst for 4 hours. The excess ethanol is then removed by distillation, the residue diluted with water and then treated with solid sodium carbonate until any acid present is removed. The title product is filtered off, washed with water and dried.

EXAMPLE VIII

Ethyl 1-Oxo-1H-6-Piperidinopyrimido[1,2-a]Quinoline-2-Carboxylate Hydrochloride

Piperidine (341 mg., 4.0 mm.) is added to a slurry of ethyl 1-oxo-1H-6-chloropyrimido[1,2-a]quinoline-2-carboxylate (605 mg., 2.0 mm.) in ethanol (15 ml.) and the mixture heated to reflux on a steam bath until a clear solution forms. The solvent is then removed under reduced pressure to leave a gummy residue.

The residue is taken up in diethyl ether (50 ml.) and the resulting solution treated with ethyl acetate saturated with hydrogen chloride. The precipitate which forms is filtered and recrystallized by dissolving it in hot ethanol (10 ml.) and adding boiling ether (40 ml.) to the solution. Upon cooling, fluffy yellow crystals precipitate. They are recovered by filtration and dried. Yield = 365 mg.; m.p. 221° C (dec.)

Analysis: Calcd. for $C_{20}H_{21}O_3N_3 \cdot HCl$: C, 61.93; H, 5.72; N, 10.83%. Found: C, 61.86; H, 5.76; N, 10.77%.

Repetition of the above procedure but using the appropriate alkyl 1-oxo-1H-6-chloropyrimido[1,2-a]quinoline-2-carboxylate reactant affords the corresponding methyl, n-propyl, isopropyl and n-butyl esters of the title compound.

Other pharmaceutically acceptable acid addition salts are prepared by substituting the appropriate acid for hydrochloric acid. The following salts are thus prepared of the above produced esters:
sulfate
citrate
acetate
butyrate
glycollate
benzoate
fumarate
tartrate
succinate
p-toluenesulfonate The esters are hydrolyzed by the procedure of Example I to afford the hydrochloride salt. Neutralization of the acid salts affords the free acid.

EXAMPLE IX

Salt Formation

The acid products of Examples I, II, III and VIII are converted to sodium, potassium, ammonium, calcium, magnesium, aluminum, triethylamine, tri-n-butylamine, piperidine, triethanolamine, diethylaminoethylamine, pyrrolidine and N,N-dibenzylethylenediamine salts by reaction with an equivalent of the appropriate metal hydroxide, ammonium hydroxide or amine in water or ethanol followed by filtration of the salt if it is insoluble or by evaporation of the solvent if the salt is soluble therein.

EXAMPLE X

Tablets

A tablet base is prepared by blending the following ingredients in the proportion by weight indicated:
Sucrose, U.S.P. —80.3
Tapioca Starch—13.2
Magnesium Stearate—6.5

Into this tablet base there is blended sufficient ethyl 1-oxo-1H-6-methoxypyrimido[1,2-a]quinoline-2-carboxylate to provide tablets containing 20, 100, and 250 mg. of active ingredient per tablet. The compositions are each compressed into tablets, each weighing 360 mg., by conventional means.

EXAMPLE XI

Capsules

Sufficient 1-oxo-1H-6-ethoxypyrimido[1,2-a]quinoline-2-carboxylic acid to provide capsules containing 2, 6, 10, 25, and 50 mg. of active ingredient per capsule is blended with the following ingredients. The compositions are filled into conventional hard gelatin capsules in the amount of 300 mg. per capsule.

| Ingredients | Weight mg./capsule |
|---|---|
| Drug | X |
| N-methylglucamine | 18.00 |
| Lactose, Anhydrous | 243.20-X |
| Corn Starch, Anhydrous | 30.00 |
| *Talc | 8.80 |

*Talc added before encapsulation.

EXAMPLE XII

Solution

A solution of n-butyl 1-oxo-1H-6-methoxypyrimido[1,2-a]quinoline-2-carboxylate is prepared with the following composition:
Effective ingredient —6.04 grams
Magnesium chloride hexahydrate —12.36 grams
Monoethanolamine —8.85 ml.
Propylene glycol —376.00 grams
Water, distilled —9.400 ml.

The resultant solution has a concentration of effective ingredient of 10 mg./ml. and is suitable for parenteral administration.

EXAMPLE XIII

Injectable Preparation

One thousand grams of ethyl 1-oxo-1H-6-methoxypyrimido[1,2-a]quinoline carboxylate are intimately mixed and ground with 2500 grams of sodium ascorbate. The ground, dry mixture is placed in vials and sterilized with ethylene oxide after which the vials are sterilely stoppered. For intravenous administration, sufficient water is added to the materials in the vials to form a solution containing 5.0 mg. of active ingredient per milliliter of injectable solution.

PREPARATION A

2-Amino-4-Hydroxyquinoline

The appropriate aniline p-toluenesulfonate and ethyl cyanoacetate are combined in equimolar quantities and heated at 225° to 260° C. until a melt required. (Higher temperatures are used if necessary to achieve a melt). The temperature of the melt is lowered to 240° to 250° C. and heating continued for 1 hour. The hot melt is poured into ice-cold chloroform (about 1 to 1.5 liters per mole of aniline reactant) and the mixture stirred for 1 hour. The solid is filtered off, added to water-ethanol (1 liter of 1:1 per mole of aniline reactant) at 45° to 50° C. and the solution made basic with ammonium hydroxide. The solid is separated by filtration and recrystallized from a suitable solvent such as isopropanol.

PREPARATION B

Ethers of 2-Amino-4-hydroxyquinoline Via Esters of p-Toluenesulfonic Acid

A mixture of the appropriate 2-amino-4-hydroxyquinoline and the appropriate lower alkyl of p-toluenesulfonate (10 to 20% molar excess) in xylene (from about 1–2 liters per mole of quinoline compound) is heated at reflux for 4–5 hours. It is then cooled, filtered and the filter cake washed with xylene. The solid is slurried in 3N KOH for 15–20 minutes and then filtered. The filter cake is washed with water, dried and recrystallized from a suitable solvent.

The 2-amino-4-lower alkoxyquinoline reactants used in the preceding examples are prepared by this general procedure.

Via Alkylation with $R_1Br$

Equimolar amounts of the appropriate 2-amino-4-hydroxyquinoline and sodium hydride are reacted in warm N,N-dimethylformamide to produce the sodio derivative of the 2-amino-4-hydroxyquinoline. An equimolar amount of the appropriate $R_1Br$ reactant is added and the reaction mixture heated for 20 minutes on a steam bath. It is then poured into water, the ether product separated by filtration or extracted with a suitable solvent such as benzene or chloroform. The extract is dried ($Na_2SO_4$) and evaporated. The products are crystallized from suitable solvents.

What is claimed is:

1. A method for the control of gastric ulcers in mammalian subjects which comprises administering to the subjects an effective antiulcer amount of a compound having the formula

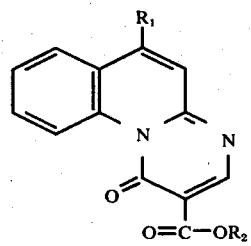

wherein $R_1$ is selected from the group consisting of alkoxy having from one to two carbon atoms and piperidino; and $R_2$ is selected from the group consisting of hydrogen and alkyl having from one to four carbon atoms; the pharmaceutically-acceptable cationic salts of those compounds wherein $R_2$ is hydrogen and the pharmaceutically-acceptable acid addition salts of those compounds wherein $R_1$ is piperidino.

2. The method according to claim 1 wherein $R_1$ is piperidino.

3. The method according to claim 1 wherein $R_1$ is alkoxy.

4. The method according to claim 3 wherein $R_1$ is ethoxy.

5. The method according to claim 3 wherein $R_1$ is methoxy.

6. The method according to claim 4 wherein $R_2$ is hydrogen.

7. The method according to claim 5 wherein $R_2$ is ethyl.

* * * * *